United States Patent
Schwiegerling

(12) 
(10) Patent No.: US 12,339,526 B2
(45) Date of Patent: *Jun. 24, 2025

(54) DIFFRACTIVE TRIFOCAL LENS

(71) Applicant: Arizona Board of Regents on Behalf of the University of Arizona, Tucson, AZ (US)

(72) Inventor: James T. Schwiegerling, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/954,376

(22) Filed: Nov. 20, 2024

(65) Prior Publication Data

US 2025/0076683 A1    Mar. 6, 2025

Related U.S. Application Data

(63) Continuation of application No. 18/213,147, filed on Jun. 22, 2023, now Pat. No. 12,164,181, which is a
(Continued)

(51) Int. Cl.
*G02C 7/04* (2006.01)
*A61F 2/14* (2006.01)
(Continued)

(52) U.S. Cl.
CPC ............ *G02C 7/041* (2013.01); *A61F 2/1451* (2015.04); *A61F 2/1613* (2013.01);
(Continued)

(58) Field of Classification Search
None
See application file for complete search history.

(56) References Cited

U.S. PATENT DOCUMENTS

| 4,210,391 A | 7/1980 | Cohen |
| 4,881,804 A | 11/1989 | Cohen |

(Continued)

FOREIGN PATENT DOCUMENTS

| DE | 69715830 T2 | 8/2003 |
| EP | 0888564 B1 | 9/2002 |

(Continued)

OTHER PUBLICATIONS

Faklis, D., and G.M. Morris, "Spectral Properties of Multiorder Diffractive Lenses," Applied Optics 34(14): 1-7, May 10, 1995.
(Continued)

*Primary Examiner* — Darryl J Collins
(74) *Attorney, Agent, or Firm* — Barry L. Davison; Davis Wright Tremaine LLP

(57) ABSTRACT

A diffractive multifocal lens is disclosed, comprising an optical element having at least one diffractive surface, the surface profile comprising a plurality of annular concentric zones. The optical thickness of the surface profile changes monotonically with radius within each zone, while a distinct step in optical thickness at the junction between adjacent zones defines a step height. The step heights for respective zones may differ from one zone to another periodically so as to tailor diffraction order efficiencies of the optical element. In one example of a trifocal lens, step heights alternate between two values, the even-numbered step heights being lower than the odd-numbered step heights. By plotting a topographical representation of the diffraction efficiencies resulting from such a surface profile, step heights may be optimized to direct a desired level of light power into the diffraction orders corresponding to near, intermediate, and distance vision, thereby optimizing the lens performance.

19 Claims, 4 Drawing Sheets

Related U.S. Application Data continuation of application No. 17/547,115, filed on Dec. 9, 2021, now Pat. No. 11,693,260, which is a continuation of application No. 16/933,106, filed on Jul. 20, 2020, now Pat. No. 11,199,725, which is a continuation of application No. 16/250,866, filed on Jan. 17, 2019, now Pat. No. 10,725,320, which is a continuation of application No. 15/136,770, filed on Apr. 22, 2016, now Pat. No. 10,209,533, which is a continuation of application No. 13/201,440, filed as application No. PCT/US2010/024165 on Feb. 12, 2010, now Pat. No. 9,320,594.

(60) Provisional application No. 61/207,409, filed on Feb. 12, 2009.

(51) Int. Cl.
*A61F 2/16* (2006.01)
*G02B 5/18* (2006.01)
*G02C 7/02* (2006.01)
*G02C 7/06* (2006.01)

(52) U.S. Cl.
CPC .......... *A61F 2/1618* (2013.01); *A61F 2/1656* (2013.01); *G02B 5/1876* (2013.01); *G02C 7/028* (2013.01); *G02C 7/042* (2013.01); *G02C 7/044* (2013.01); *G02C 7/049* (2013.01); *A61F 2/14* (2013.01); *G02C 2202/20* (2013.01)

(56) References Cited

U.S. PATENT DOCUMENTS

| | | |
|---|---|---|
| 4,936,666 A | 6/1990 | Futhey |
| 4,995,714 A | 2/1991 | Cohen |
| 5,117,306 A | 5/1992 | Cohen |
| 5,121,980 A | 6/1992 | Cohen |
| 5,122,903 A | 6/1992 | Aoyama |
| 5,178,636 A | 1/1993 | Silberman |
| 5,344,447 A | 9/1994 | Swanson |
| 5,699,142 A | 12/1997 | Lee |
| 6,120,148 A | 9/2000 | Fiala |
| 6,951,391 B2 | 10/2005 | Morris |
| 7,025,456 B2 | 4/2006 | Morris |
| 7,232,218 B2 | 6/2007 | Morris |
| 7,441,894 B2 | 10/2008 | Zhang |
| 10,209,533 B2 | 2/2019 | Schwiegerling |
| 2006/0055883 A1 | 3/2006 | Morris |
| 2006/0098162 A1 | 5/2006 | Bandhauer |
| 2006/0098163 A1 | 5/2006 | Bandhauer |
| 2006/0116764 A1 | 6/2006 | Simpson |
| 2007/0182924 A1 | 8/2007 | Hong |
| 2011/0267693 A1 | 11/2011 | Kobayashi |

FOREIGN PATENT DOCUMENTS

| | | |
|---|---|---|
| EP | 1279992 A2 | 1/2003 |
| EP | 1884219 A2 | 2/2008 |
| EP | 1891912 A1 | 2/2008 |
| EP | 2045648 A1 | 4/2009 |
| EP | 2377493 A1 | 10/2011 |
| EP | 2378319 A1 | 10/2011 |
| IE | 68759 B1 | 7/1996 |
| JP | 02-137815 A | 5/1990 |
| JP | 08-507158 A | 7/1996 |
| JP | 2000-511299 A | 8/2000 |
| JP | 2006-139246 A | 6/2006 |
| JP | 2010-158315 A | 7/2010 |
| JP | 4551489 B2 | 9/2010 |
| KR | 10-2008-0009126 A | 1/2008 |
| RU | 2303961 C1 | 8/2007 |
| WO | 1994/017435 A1 | 8/1994 |
| WO | 2003/107076 A1 | 12/2003 |
| WO | 2006/060480 A2 | 6/2006 |
| WO | 2010/079528 A1 | 7/2010 |
| WO | 2010/079537 A1 | 7/2010 |

OTHER PUBLICATIONS

Australian Statement of Grounds and Particulars in Opposition mailed Jan. 11, 2016, in Australian Patent Application No. 2010213535, filed Feb. 12, 2010, 28 pages.

European Third Party Observations dated Aug. 18, 2016, filed in European Patent Application No. 10741835.2, filed Feb. 12, 2010, 3 pages.

European Examination Report dated Aug. 18, 2017, issued in European Patent Application No. 10 741 835.2-1651, filed Feb. 12, 2010, 7 pages.

Extended European Search Reported dated Aug. 7, 2020, issued in European Patent Application No. 20154708.0, filed Feb. 12, 2010, 8 pages.

International Search Report and Written Opinion mailed Sep. 27, 2010, issued in International Patent Application No. PCT/US2010/024165, filed Feb. 12, 2010, 8 pages.

DIFFRACTIVE TRIFOCAL LENS

CROSS REFERENCE TO RELATED APPLICATIONS

This patent application is a continuation of U.S. patent application Ser. No. 18/213,147, filed Jun. 22, 2023, now U.S. Pat. No. 12,164,181, which is a continuation of U.S. patent application Ser. No. 17/547,115, filed Dec. 9, 2021, now U.S. Pat. No. 11,693,260, which is a continuation of U.S. patent application Ser. No. 16/933,106, filed Jul. 20, 2020, now U.S. Pat. No. 11,199,725, which is a continuation of U.S. patent application Ser. No. 16/250,866, filed Jan. 17, 2019, now U.S. Pat. No. 10,725,320, which is a continuation of U.S. patent application Ser. No. 15/136,770, filed Apr. 22, 2016, now U.S. Pat. No. 10,209,533, which is a continuation of U.S. patent application Ser. No. 13/201,440, filed Aug. 12, 2011, now U.S. Pat. No. 9,320,594, which is a 371 National Phase Application of International Patent Application No. PCT/US2010/024165, filed Feb. 12, 2010, which claims the benefit of U.S. Provisional Patent Application No. 61/207,409, filed Feb. 12, 2009, the disclosures of which are hereby incorporated by reference in their entirety.

TECHNICAL FIELD

The present invention relates generally to the field of diffractive optics and ophthalmology, and more specifically, to the design and construction of corrective multifocal intraocular or contact lenses useful for treating presbyopia.

BACKGROUND

Bifocal and trifocal contact lenses are commonly used to treat presbyopia, a condition in which the eye exhibits a progressively diminished ability to focus on near objects. Human beings become presbyopic due to aging, and the effect typically becomes noticeable starting at about the age of 40-45 years, when they discover they need reading glasses. Presbyopic individuals who wear corrective lenses may then find that they need two separate prescriptions, preferably within the same bifocal lens, one for reading (near) and another for driving (distance). A trifocal lens further improves vision at intermediate distances, for example, when working at a computer. An intraocular lens (IOL) is an artificial replacement lens that may be used as an alternative to a contact lens or eyeglasses. An IOL is often implanted in place of the natural eye lens during cataract surgery. An intracorneal lens (ICL) is an artificial lens that is implanted into the cornea.

Conventional corrective optics are typically refractive lenses, meaning that they bend and focus light rays reflected from an object to form a focused image of the object on the retina. The bending of the light rays is dictated by Snell's law which describes the degree of bending that occurs as light rays cross the boundary of two materials with distinct indices of refraction.

Diffractive lenses have a repeating structure that may be formed in the surface of an optical element by a fabrication method such as, for example, cutting the surface using a lathe that may be equipped with a cutting head made of a hard mineral such as diamond or sapphire; direct write patterning using a high energy beam such as a laser beam or electron beam or a similar method of ablating the surface; etching the surface using a photolithographic patterning process; or molding the surface. The diffractive structure is typically a series of concentric annular zones, which requires each zone to become progressively narrower from the center to the edge of the lens. There may be, for example, 20-30 zones between the center and the edge of the lens. The surface profile within each zone is typically a smoothly varying function such as an arc, a parabola, or a line. At the outer periphery of each zone there is a discrete step in the vertical surface profile, the step height typically measuring about 0.5-3 microns. The resulting surface structure acts as a circularly symmetric diffraction grating that disperses light into multiple diffraction orders, each diffraction order having a consecutive number, zero, one, two, and so forth.

"Diffraction efficiency" refers to the percentage of incident light power transmitted into each of the various diffractive orders comprising the diffraction pattern at the focal plane. If the zones have equal surface areas and are radially symmetric, they focus light of different diffraction orders onto the optical axis of the lens, each diffraction order having its own distinct foci. Thus, the diffractive lens acts as a multifocal lens having many discrete foci. For example, a diffractive bifocal lens simultaneously provides sharp retinal images of objects at two different distances, as well as two corresponding out-of-focus images. The human visual system has the ability to select from among the different retinal images, thereby enabling simultaneous multifocal vision using a single diffractive lens.

Diffractive lenses may be used as contact lenses and IOLs for correcting presbyopia. In such an application, the lens comprises one refractive surface and one diffractive surface. In practice, the light energy passing through a diffractive lens is typically concentrated into one, two, or three diffractive orders, while contributing an insignificant amount of light energy to other diffractive orders. With respect to diffractive corrective lenses, for example, a high diffraction efficiency for the zeroth order connotes a greater improvement in visibility at far distances. The amount of optical energy directed into each diffraction order is dictated by the zonal step heights. A lens designer may choose, for the diffractive surface features of a bifocal lens, step heights so as to introduce, for example, a one-half wavelength phase change between adjacent zones, which directs approximately 40% of the incident light into the zeroth diffraction order corresponding to distance vision, and 40% into the positive first diffractive order, corresponding to near vision. The remaining 20% of the incident light in a conventional bifocal lens is directed to other diffraction orders that are not useful for vision.

Existing designs for multifocal intraocular and contact lenses use either refractive optics, a combination refractive/diffractive design, or diffractive lenses that direct light into a single diffractive order. For example, U.S. Pat. No. 5,344,447 to Swanson, discloses a trifocal IOL design that enhances distance vision using a combination lens having a refractive surface and a diffractive surface. Each diffractive zone in this case corresponds to a binary step. This lens distributes light approximately equally between the positive first, zeroth, and negative first diffraction order. However, a drawback to this configuration is that excess light is directed into other higher diffractive orders, reducing visual quality. Furthermore, this configuration makes the power of the underlying carrier lens more difficult to predict because distance vision is dictated by a combination of the lens' refractive power with the diffractive power of the minus one diffractive order. None of the existing alternatives succeeds in directing enough light into a diffractive order that corresponds to an intermediate focal distance, and therefore trifocal contact lenses and IOLs fail to perform equally well throughout the full focal range. For example, U.S. Pat. No.

7,441,894, issued to Zhang, et al. discloses a trifocal intraocular lens having diffractive zones of varying areas capable of directing about 25-28% of incident light into the near and far foci, but only about 10% of the incident light is directed into the intermediate focus.

SUMMARY

A diffractive multifocal lens is disclosed, comprising an optical element having at least one diffractive surface, the surface profile of which comprises a plurality of concentric annular zones. The optical thickness of the radial surface profile changes monotonically within each zone. A distinct step in optical thickness occurs at the outer periphery of each zone, the size of which is referred to as a "step height." According to a preferred embodiment, instead of being equal, the step heights for adjacent zones differ from one zone to another periodically so as to tailor diffraction order efficiencies of the optical element. There is particular interest in increasing at least the first order diffraction efficiency of the optical element to address intermediate distance vision for trifocal lenses.

In one example of a trifocal lens, the step heights alternate between two values, the even-numbered step heights being lower than the odd-numbered step heights. In alternative embodiments, the even-numbered step heights may be higher than the odd-numbered step heights, or successive step heights may alternate between three or more values. In still another embodiment, the pattern of step heights gradually changes from the center to the edge of the lens. According to one such embodiment, the center of the lens is trifocal, but it becomes progressively bifocal toward the edge of the lens. By modeling and plotting a topographical representation of the diffraction efficiencies resulting from such a surface profile, dimension parameters such as step height values may be selected so as to achieve directing a desired proportion of light power into designated diffraction orders, thereby optimizing the distance, intermediate, and near performance of the multifocal lens.

It is to be understood that this summary is provided as a means for generally determining what follows in the drawings and detailed description, and is not intended to limit the scope of the invention. Objects, features and advantages of the invention will be readily understood upon consideration of the following detailed description taken in conjunction with the accompanying drawings.

DETAILED DESCRIPTION OF EMBODIMENTS OF THE INVENTION

Figure 1:
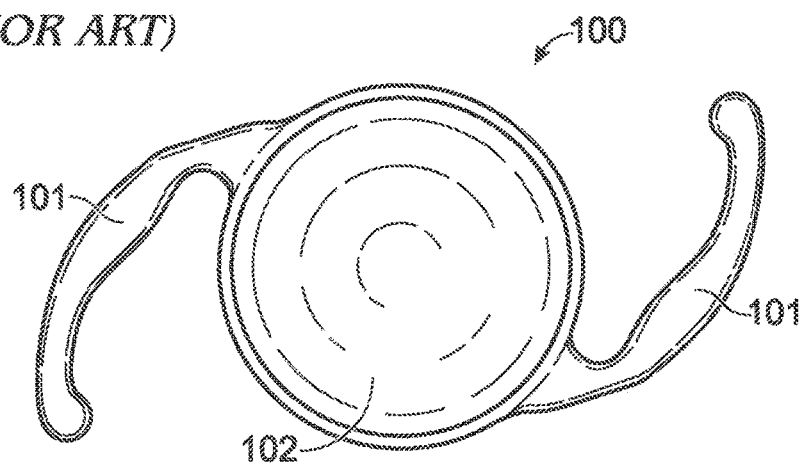
FIG. 1 shows a commercially available prior art diffractive bifocal intraocular lens.

The present invention will be readily understood by the following detailed description in conjunction with the accompanying drawings. To facilitate this description, like reference numerals designate like structural elements. In the following description many details are set forth to provide an understanding of the disclosed embodiments of the invention. However, upon reviewing this disclosure, it will become apparent to one skilled in the art that not all of the disclosed details may be required to practice the claimed invention and that alternative embodiments might be constructed without departing from the principles of the invention.

Figure 2:
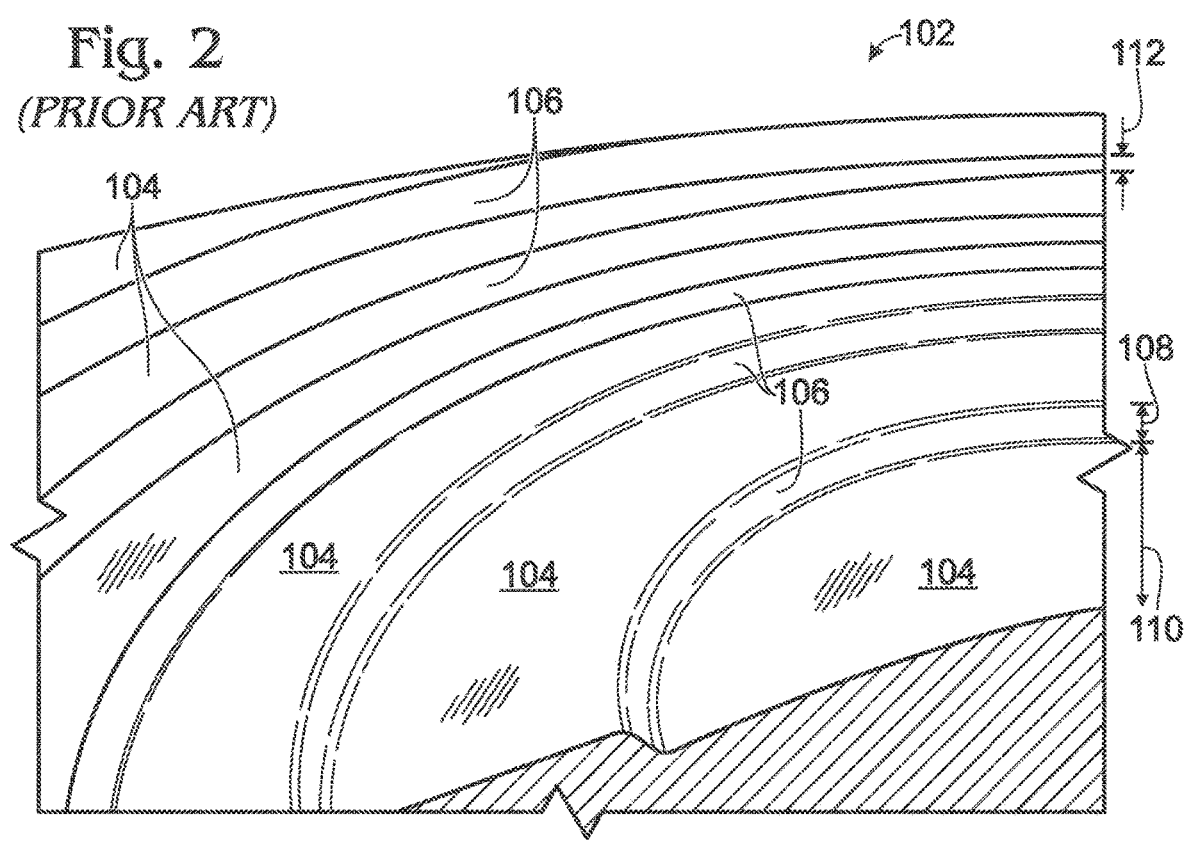
FIG. 2 is a magnified view of the surface of a central zone of the prior art diffractive bifocal intraocular lens shown in FIG. 1, in which the center of the lens is located at the lower right hand corner of the image.

Referring to FIG. 1, an existing diffractive bifocal intraocular lens 100 is shown. Lens 100 is commercially known as a ReSTOR® lens implant, and is available from Alcon Laboratories, Inc. of Fort Worth, Texas. The lens implant comprises a pair of extensions 101 connected to a central optical element having at least one optical surface 102 in which a diffractive profile pattern is formed within radial zones. FIG. 2 shows a magnified view of optical surface 102, in which a generally radially symmetric surface profile pattern for a series of concentric annular zones 104 features, at the outer periphery of each zone, a discrete step 106, having step height 108. The widths of zones 104 generally decrease from the center toward the edge of lens 100 so that a central zone width 110 may be significantly wider than an edge zone width 112. Zones of different widths preferably represent equal surface areas. In general, if the step height 108 introduces a phase delay of $2\pi$, a single power lens results, i.e., the lens will have a single focus; if the step height 108 introduces a phase delay not equal to a multiple of $2\pi$, a bifocal lens results.

Figure 3:
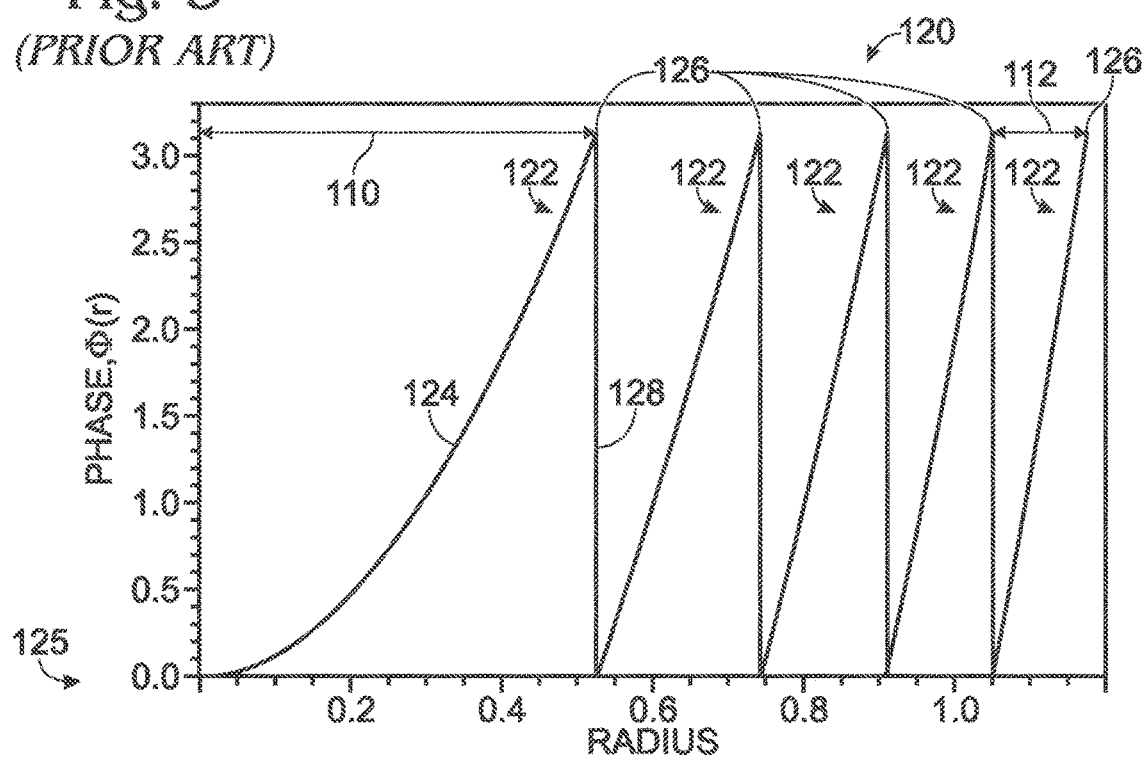
FIG. 3 is a plot of the optical phase change introduced by a conventional prior art bifocal diffractive lens as a function of radius across five zones of the lens, showing generally equal step heights.

FIG. 3 shows a radial profile 120 of the optical phase change experienced by an incident light wave as it passes through the diffractive lens 100. Radial profile 120 may be achieved by diffractive structures generally having sawtooth-shaped elements, or by varying the index of refraction of the lens material. The radial dependence of the phase change $\Phi(r)$ is given by $$\Phi(r) = 2\pi\alpha p \left[ j - r^2 / (2p\lambda_o F_o) \right] \tag{1}$$

$\alpha = \lambda/\lambda_o$ [n($\lambda$)−n'($\lambda$)]/[n($\lambda_o$)−n'($\lambda_o$)], for radii r within the $j^{th}$ zone (2) in which $\lambda_o$ is the design wavelength, i.e., the wavelength at which a phase change of $2\pi$ occurs at each zone boundary; n is the index of refraction of the lens material; $F_o$ is the focal length when the illumination wavelength $\lambda = \lambda_o$; n' is the index of refraction of the material surrounding the lens; and p is an integer that represents the maximum phase modulation as a multiple of $2\pi$. The cross-section of the actual optical surface, corresponding to the concentric regions 104 shown in FIG. 2 is related to the radial phase change profile. The corresponding maximum height of the surface relief of optical surface 102 is given by $$h_{max}(r) = p\lambda_o / [n(\lambda_o) - n'(\lambda_o)] \qquad (3)$$

and is typically about 5 microns.

Referring to FIG. 3, elements of radial phase profile 120 have a sawtooth shape 122, characterized by sharp peaks having a leading edge 124 that rises from a first value 125 normalized to zero, gradually to a peak value 126, and a trailing edge 128 that falls abruptly from the peak value 126 back to the initial height 125. The central ring width 110 corresponds to the radius of the first peak, and the edge ring width 112 corresponds to the distance between the fourth and fifth peaks in this example, in which peak values 126 are associated with substantially equal step heights. The radial phase profile of FIG. 3 is produced by a surface profile, the elements of which have a similar shape as sawtooth 122, and which have an associated optical thickness profile that also has a similar shape as sawtooth 122. Existing bifocal intraocular lenses 100 in this configuration typically have diffraction efficiencies of 40% into each of the zeroth and first diffractive orders (far and near distances, respectively), and substantially smaller diffraction efficiencies for higher diffractive orders. As a result, distance and near vision are enhanced, but intermediate vision is limited.

Figure 4:
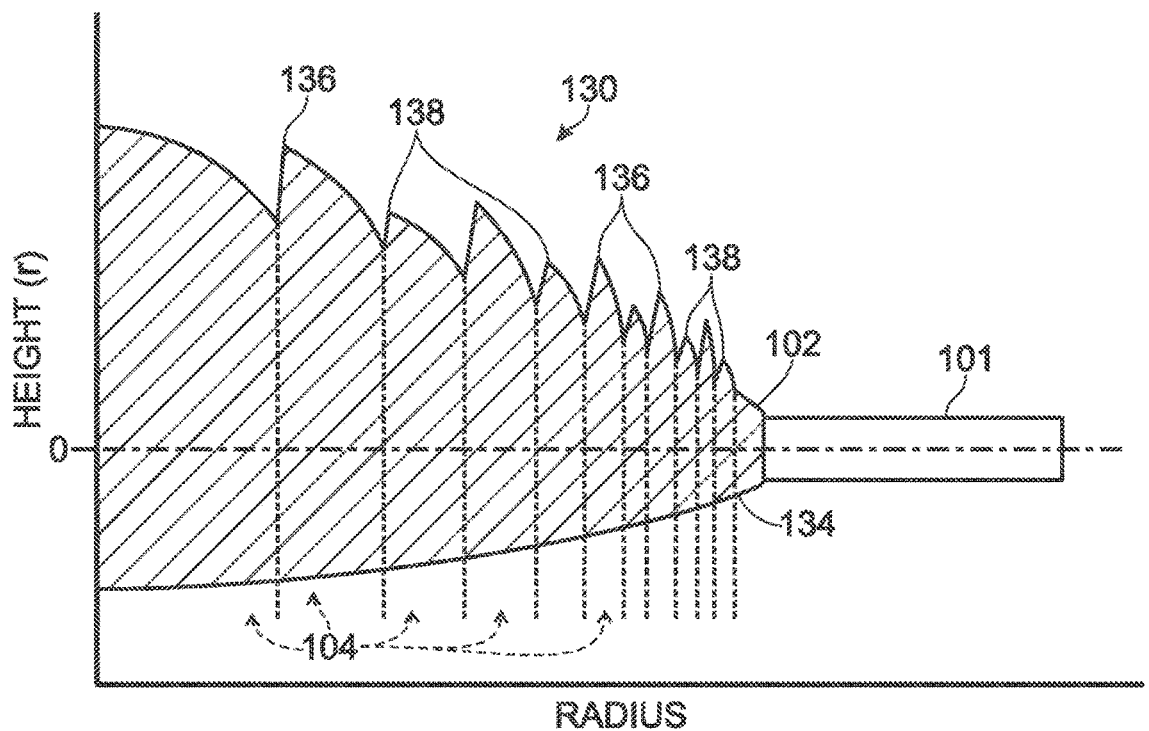
FIG. 4 is a cross-sectional view of the radial surface profile for a diffractive structure according to a preferred embodiment of a novel trifocal diffractive lens, showing two alternating step heights.

FIG. 4 shows a cross-sectional view of a physical surface profile 130 of a diffractive structure fabricated in an upper optical surface 102 of a lens according to a preferred embodiment. A lower surface of the lens, 134, is a refractive surface. The radial width of each diffractive annular zone 104 decreases from the center of the lens to the edge of the lens to maintain equal areas of the diffractive zones. The step heights between each zone alternate between two values, starting with the larger step height 136 for the transition between the central zone and the first annular zone. A smaller step height 138 characterizes the transition between the first and second zones. This alternating step height pattern is repeated out to the edge of the lens.

Figure 5:
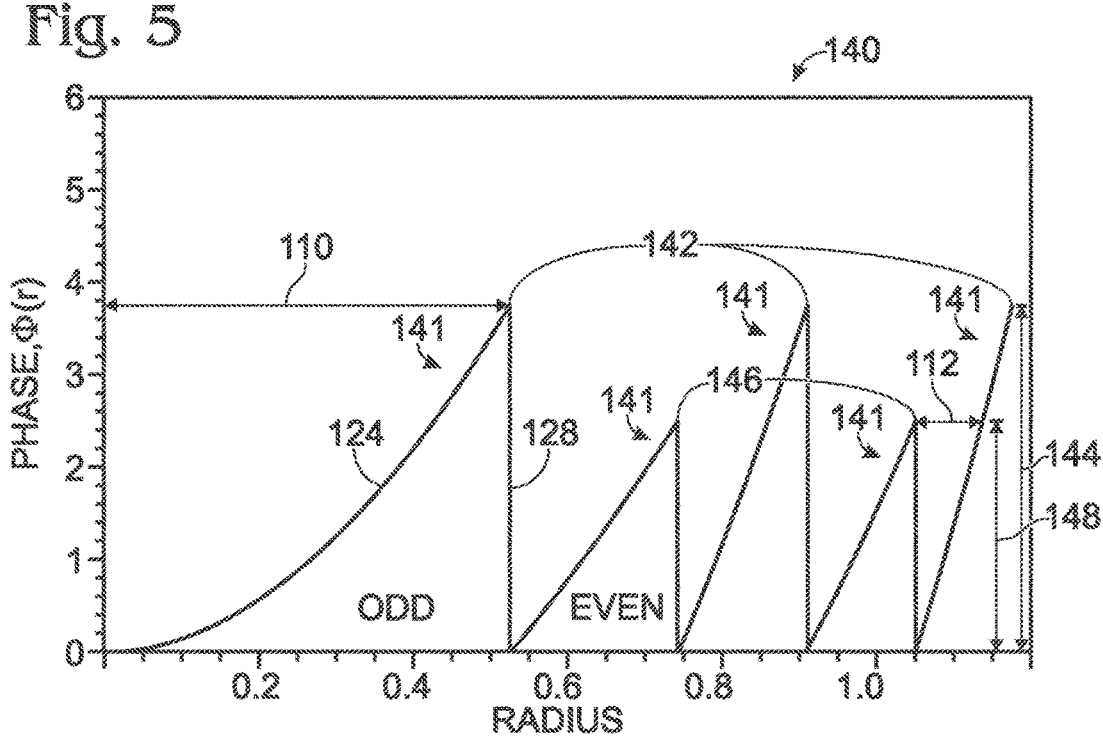
FIG. 5 is a plot of the optical phase change introduced by the diffractive structure shown in FIG. 4, as a function of radius, showing corresponding alternating step heights for five representative zones.

FIG. 5 shows a plot of the radial profile 140 of the optical phase change $\Phi(r)$ experienced by an incident light wave as it passes through an enhanced diffractive trifocal lens having the surface profile shown in FIG. 4. Elements of radial profile 140 have a sawtooth shape 141 similar to sawtooth shape 122, in which each of the concentric zones is located at the same radius, but the step heights are not all substantially equal. Instead, a first set of peaks 142, having larger step heights 144, alternate with a second set of peaks 146 having smaller step heights 148. These features of the phase profile correspond to surface profile step heights 136 and 138, respectively. By alternating the step heights incident light power may be directed to the diffractive orders corresponding to distance, intermediate, and near vision. According to a preferred embodiment exemplified below, odd-numbered step heights are greater than even-numbered step heights, though in alternative embodiments, the reverse may be stipulated, while applying the same methodology for optimizing the design.

Figure 6:
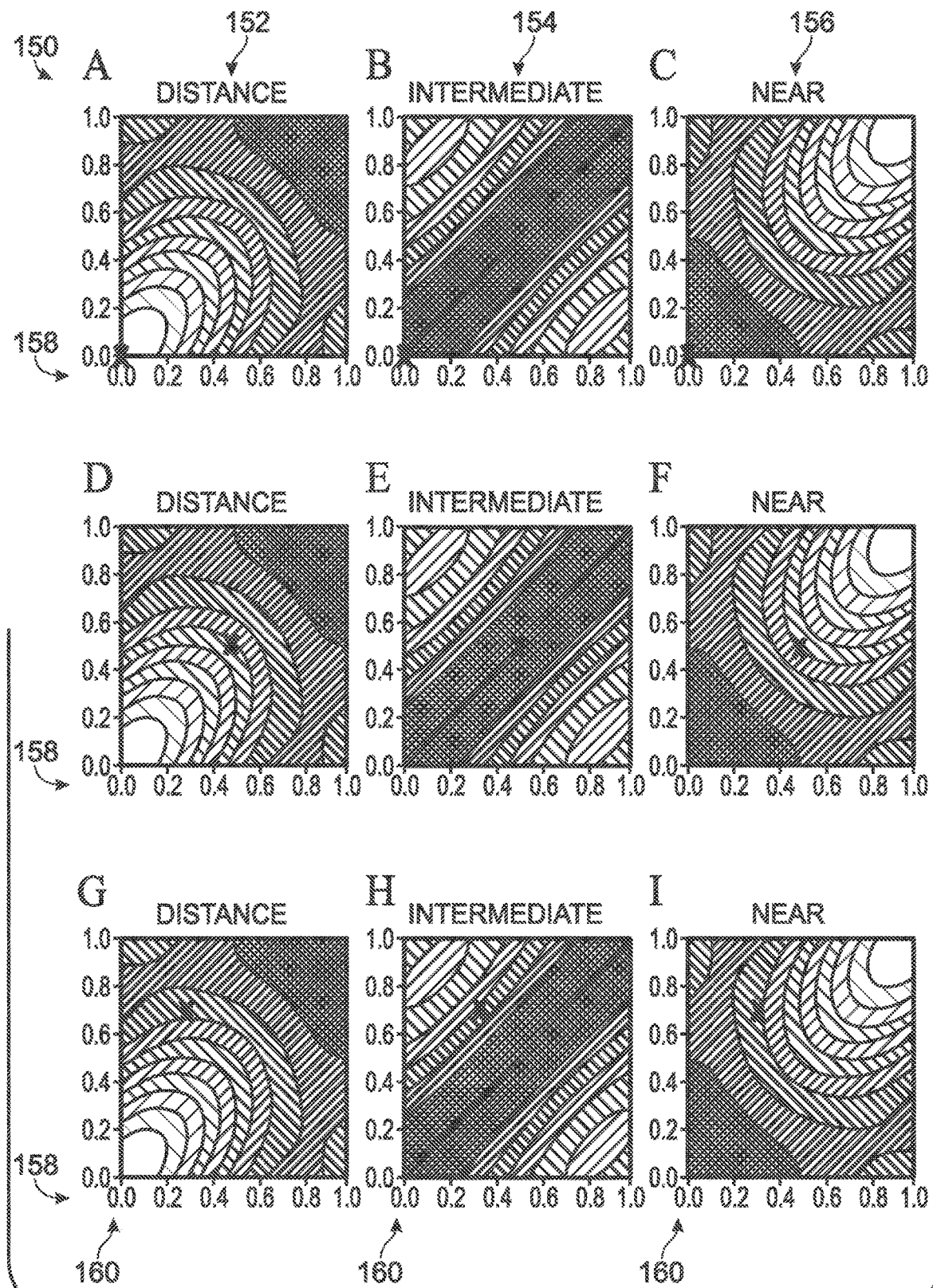
FIG. 6 is a series of computer-generated two-dimensional topographic plots showing diffraction efficiencies that result from different choices of values for the alternating step heights in the optical phase profile of FIG. 5.

FIG. 6 shows nine computer-generated topographic plots A-I of diffraction efficiencies for light power directed into the zeroth, +first, and +second diffraction orders. These diffraction orders represent distance vision 152, intermediate vision 154, and near vision 156, respectively for a diffractive multifocal lens having a generalized sawtooth-shaped phase profile consistent with both FIGS. 3 and 5, for which odd-numbered step heights and even-numbered step heights may take on different values.

An expression for calculating diffraction efficiencies for the phase profile of FIG. 5 is derived by generalizing a scheme disclosed in an article by Faklis and Morris (Dean Faklis and G. Michael Morris, "Spectral Properties of Multiorder Diffractive Lenses," Applied Optics, Vol. 34, No. 14, May 10, 1995), of which sections 1 and 2 are hereby incorporated by reference. Faklis and Morris present diffraction efficiencies relevant to the phase profile of FIG. 3 by deriving an expression for the diffraction efficiency of the $m^{th}$ diffracted order, $\eta_m$, by expanding the amplitude transmission function of the diffractive lens as a Fourier series, and extracting the Fourier coefficient, $c_m$. The diffraction efficiency, nm, is then given by $|c_m|^2$. For a phase profile having substantially equal step heights, Faklis and Morris show that the diffraction efficiency may be expressed as $$\eta_m = [\sin[\pi(\alpha p - m)] / \pi(\alpha p - m)]^2. \qquad (4)$$

By generalizing this derivation, it may be shown that the diffraction efficiency for the $m^{th}$ diffracted order for the phase profile of FIG. 5, having two dimension parameters (e.g., alternating step heights) A1 and A2, is given by:

$$\eta_m(m, p, \alpha, A1, A2) = sqrt\{1/4\{\text{sinc}\,[\pi/2(m - 2A1p\alpha)]^2 + \qquad (5)$$
$$2(-1)^m \cos[\pi(A1 - A2)p\alpha]\,\text{sinc}\,[\pi/2(m - 2A1p\alpha)]$$
$$\text{sinc}\,[\pi/2(m - 2A2p\alpha)] + \text{sinc}[\pi/2(m - 2A2p\alpha)]^2\}\}.$$

A similar derivation may be performed for a lens design having three or more different step heights, yielding a different expression analogous to (5) for the specific example disclosed herein.

Referring to FIG. 6, a graph of $\eta_m$ for m=0 is shown in plots A, D, and G; a graph of $\eta_m$ for m=+1 is shown in plots B, E, and H; and a graph of $\eta_m$ for m=+2 is shown in plots C, F, and I. In each of the nine plots, horizontal axes 158 represent step heights of even numbered profile peaks, normalized to $2\pi$, and vertical axes 160 represent step heights of odd numbered profile peaks, normalized to $2\pi$. The nine plots thus each provide a topographic "map" on which may be located points of interest marked with an "X" corresponding to examples of different diffractive lens designs, dictated by the choice of step heights A1 and A2. The maps thus indicate, by their relative shading at the point of interest, the amount of power directed into each focal region to yield different proportions of distance, intermediate, and near vision. For example, step heights A1 and A2 may be chosen so as to enhance the diffraction efficiencies for all three foci equally, or they may be chosen so that the zeroth order diffraction efficiency is twice that of the +first and +second orders, which would yield better distance vision, at the expense of intermediate vision. The lightest shaded regions in each plot correspond to 100% diffraction efficiency, and the darkest shaded regions in each plot correspond to 0% diffraction efficiency. (A similar set of plots may be generated for a lens design having three or more different step heights, A1, A2, and A3, according to a corresponding expression derived in a similar fashion as (5) above.)

Topographic plots A, B, and C in FIG. 6 illustrate a limiting case in which both the odd and even phase step heights 126, represented by variables A1 and A2, are set to zero, i.e., this case represents the absence of a diffractive surface pattern, which is essentially a refractive lens. Plotting the point (0,0) on each of topographic plots A, B, and C yields an "X" in the lower left corner of the topographic field. In plot A, the X coincides with a bright spot, indicating that about 100% of the light is directed into the zeroth "diffraction order" (distance); in plots B and C, the X coincides with a dark region indicating that substantially no light is directed into the first and second diffraction orders (intermediate and near), consistent with the absence of a multifocal diffraction pattern in this example.

Topographic plots D, E, and F in FIG. 6 illustrate the limiting case corresponding to a conventional bifocal diffractive lens, having the profile shown in FIG. 3, in which both the odd and even step heights 126, represented by variables A1 and A2, are equal to $0.5*2\pi$. Plotting coordinates (0.5, 0.5) yields an "X" near the center of each plot. In plots D and F, the X coincides with a grey region, indicating that substantially equal portions of light power are directed into the zeroth and second diffraction orders corresponding to distance and near vision. In plot E, the X coincides with a dark region, indicating that substantially 0% of the light power is directed to the first diffractive order, corresponding to intermediate vision.

Topographic plots G, H and I in FIG. 6 illustrate a preferred embodiment of a multistep diffractive lens shown in FIG. 5. In this example, odd step heights 136 are assigned a value $0.7*2\pi$ and even step heights 138 are assigned a value $0.3*2\pi$, to yield optimal results. The reason for assigning these values can be appreciated by plotting the point (0.3, 0.7) on each of topographic plots G, H and I, which yields an "X" in the upper left quadrant of each plot. In each of the plots, the X coincides with a light grey-shaded region, the greyscale value indicating that the light power is directed equally into each of the zeroth, first, and second diffractive orders, so that distance, intermediate, and near vision are all substantially equally enhanced.

Figure 7:
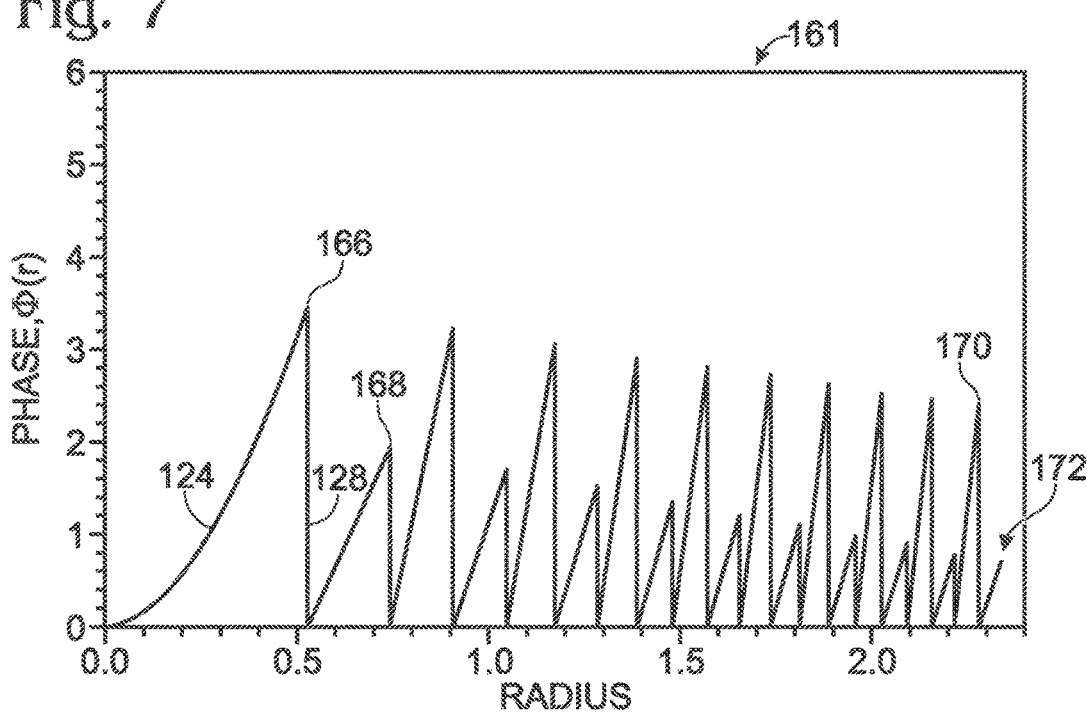
FIG. 7 is a plot of the optical phase change introduced by a graduated trifocal/bifocal diffractive structure as a function of radius, showing corresponding alternating step heights.

A more complex design example, for which a gradually decreasing phase profile is shown in FIG. 7, provides a trifocal portion in the center of the lens, progressing to a bifocal lens at the edge of the lens. According to this embodiment, a pair of alternating step heights decrease monotonically from first prescribed values 166 and 168 at the center of the lens to second prescribed values 170 and 172 at the edge of the lens. For example, step height values A1 and A2 may be chosen to be $0.3\lambda$ and $0.7\lambda$ at the center of the lens, and $0.1\lambda$ and $0.45\lambda$ at the edge of the lens respectively. A trifocal lens fabricated according to such a design would provide enhanced distance, intermediate, and near vision for a person having small pupils, and it would favor distance and intermediate vision for a person having large pupils, gradually reducing the near vision for large pupils. Visually, this would allow a person in bright lighting conditions to drive, see a computer monitor, and read, while under dark conditions when there is no need to read, it would allow the person to drive and see a dashboard more clearly.

Although certain embodiments have been illustrated and described herein, it will be appreciated by those of ordinary skill in the art that a wide variety of alternative or equivalent embodiments or implementations calculated to achieve the same purposes may be substituted for the embodiments illustrated and described without departing from the scope of the present invention. Those with skill in the art will readily appreciate that embodiments in accordance with the present invention may be implemented in a very wide variety of ways. This application is intended to cover any adaptations or variations of the embodiments discussed herein.

The terms and expressions which have been employed in the foregoing specification are used therein as terms of description and not of limitation, and there is no intention, in the use of such terms and expressions, to exclude equivalents of the features shown and described or portions thereof, it being recognized that the scope of the invention is defined and limited only by the claims that follow.

The invention claimed is:

1. A diffractive multifocal lens comprising an optical element having a first diffractive optical surface having a radial surface profile having a diffractive structure comprising a plurality of concentric annular zones concentric with a central zone, wherein the optical thickness of the lens changes monotonically within each zone, a distinct step in optical thickness occurs at the junction between the zones, height of the steps differs between each adjacent zones, and a pattern of step height differences between two or more adjacent zones repeats radially from the central zone of the lens so as to tailor the proportions of the diffraction order efficiencies of at least three orders of the radial surface profile of the optical element corresponding to distance, intermediate, and near vision, wherein the lens has a radial phase profile of the optical phase change introduced by the diffractive structure, and elements of the radial phase profile within each of the concentric annular zones comprise a peak having a leading edge that rises from a first value, to a peak value, and a trailing edge that falls from the peak value back towards the first value.

2. The lens of claim 1, wherein the plurality of concentric annular zones is concentric with the central zone and assignable, from an outer edge of the central zone toward an edge of the lens, as alternating odd and even numbered zones, and wherein the step heights of the even numbered zones are greater than the step heights of the odd numbered zones.

3. The lens of claim 2, wherein the difference in step heights between two adjacent zones gradually changes from the center to the edge of the lens.

4. The lens of claim 1, wherein the plurality of concentric annular zones is concentric with the central zone and assignable, from an outer edge of the central zone toward an edge of the lens, as alternating odd and even numbered zones, and wherein the step heights of the even numbered zones are less than the step heights of odd numbered zones.

5. The lens of claim 4, wherein the difference in step heights between two adjacent zones gradually changes from the center to the edge of the lens.

6. The lens of claim 1, wherein the step heights of at least three radially successive zones differ from one another.

7. The lens of claim 6, wherein the three or more step heights change gradually from the center to the edge of the lens.

8. The lens of claim 1, wherein the step heights are chosen so that the diffraction efficiencies of at least the zeroth, positive first, and positive second orders are substantially equal.

9. The lens of claim 1, wherein a projected area of each consecutive zone is substantially constant.

10. The lens of claim 1, wherein the radial surface profile height of each zone forms an arc.

11. The lens of claim 1, wherein the radial surface profile height of each zone increases substantially linearly.

12. The lens of claim 1, further comprising a second optical surface that is a refractive optical surface separated from the first optical surface.

13. The lens of claim 1, wherein the difference in step heights between two adjacent zones gradually changes from the center to the edge of the lens.

14. The lens of claim 1, adapted to be worn as a contact lens.

15. The lens of claim 1, adapted to be surgically implanted as an intraocular lens.

16. The lens of claim 1, wherein the lens comprises an intracorneal implant.

17. A method of making a diffractive multifocal lens, comprising:
    modeling an optical element having a first diffractive optical surface having a radial surface profile having a diffractive structure according to claim 1;
    calculating from the model a diffractive efficiency distribution for light propagating through the patterned optical element;
    selecting dimension parameters according to the diffractive efficiency distribution, so as to achieve desired diffractive efficiencies for at least three corresponding diffraction orders of the lens; and
    forming on the surface of an optical substrate the periodic surface profile pattern including the selected dimension parameters.

18. The method of claim 17, wherein forming the surface profile pattern comprises shaping a surface of the optical element using a lathe, a mold, an energy beam, etching, or ablating.

19. The lens of claim 1, wherein elements of the radial phase profile within each of the concentric annular zones have a sawtooth shape, comprising a sharp peak having a leading edge that rises from a first value normalized to zero, gradually to a peak value, and a trailing edge that falls abruptly from the peak value back to the first value.

* * * * *